United States Patent [19]
Green et al.

[11] Patent Number: 5,902,800
[45] Date of Patent: May 11, 1999

[54] DEXTRAN FORMULATIONS AND METHOD FOR TREATMENT OF INFLAMMATORY JOINT DISORDERS

[75] Inventors: June Ha Green, Cheshire, United Kingdom; Peter B. Buckley, Uppsala, Sweden

[73] Assignee: Glenpharma, Uppsala, Sweden

[21] Appl. No.: 09/049,055

[22] Filed: Mar. 27, 1998

[51] Int. Cl.$^6$ .......................... A61K 31/715; C08B 37/02
[52] U.S. Cl. ............................... 514/59; 536/112
[58] Field of Search ......................... 514/54, 59; 536/112

[56] References Cited

FOREIGN PATENT DOCUMENTS 0 331 471 A1   9/1989   European Pat. Off. .
92/13541       8/1992   WIPO .

OTHER PUBLICATIONS

Barghouthi et al., "Inhibition by Dextran of Pseudomonas aeruginosa Adherence to Epithelial Cells", Am. J. Respir. Crit. Care Med., vol. 154(6): 1788–1793, 1996.
Timsit et al. "Proprietes anti–inflammatoires et anticomplementaires de dextrans de poids moleculaires varies", C.R. Seances Soc. Biol. Fil., vol. 165(2): 268–273, 1971.
de Belder, Anthony N. "Medical Applications of Dextran and Its Derivatives" from Polysaccharides in Medicinal Chemistry, ed. by Severian Dumitriu, publ. by Marcel Dekker, Inc., pp. 505–523, 1996.
Albuquerque, M., et al., "Articular Lymphoscintigraphy in Human Knees Using Radiolabeled Dextran," Lymphology 23 (1990), pp. 215–218.
Arfors, K., et al., "Pharmacological Characteristics of Artificial Colloids," Bailliere's Clin. Anaesthesiol., vol. 11, No. 1, 1997, pp. 15–47.
Green, J., "Macrodex and Arthritic Joints," J. Orthopaedic Med., 19 (1) Apr. 1997, 27–28.
Grennan, D.M., et al., "The Effects of Prostaglandin $E_1$, Bradykinin and Histamine on Canine Synovial Vascular Permeability," Br. J. Pharmac., 1977, 60, pp. 251–254.
Jurvelin, J.S. et al., "Effects of Different Irrigation Liquids and Times on Articular Cartilage: An Experimental, Biomechanical Study," Arthroscopy: J. Arthroscop. & Related Surgery, 10(6), 1994, pp. 667–672.
Menger, M.D., "Microcirculatory Disturbances Secondary to Ischemia–Reperfusion," Transplant. Proceed., vol. 27, No. 5 (Oct. 1995), pp. 2863–2865.
Hedin, H., et al., "Incidence, Pathomechanism and Prevention of Dextran–Induced Anaphylactoid/Anaphylactic Reactions in Man," Develop. Biol. Standard., 48, (1980) pp. 179–189.
Moreno, J.L., et al., "Articular Irrigation in Arthroscopic Procedures," Int. Ortopaedics (SICOT), 1986, 10, pp. 101–104 (w/English summary).
Smith, M.M., "The Effects of Some Polysulphated Polysaccharides on Hyaluronate (HA) Synthesis by Human Synovial Fibroblasts," Agents & Actions Supplements, vol. 18, 1986, pp. 55–62.

*Primary Examiner*—Howard C. Lee
*Attorney, Agent, or Firm*—McDermott, Will, Emery

[57] ABSTRACT

This disclosure describes pharmaceutical compositions and a method for treatment of joint inflammation and pain bought about by e.g. arthritis, physical trauma, bacterial or viral infection. In one embodiment, the method comprises administration of a bimodal molecular weight dextran formulation comprising 0.2 to 32% w/v of a dextran fraction with average molecular weight between 30,000 and 110,000 daltons and 0.2 to 6% dextran with an average molecular weight between 500 and 3,000 daltons, into the joint of a warm blooded animal.

8 Claims, No Drawings

DEXTRAN FORMULATIONS AND METHOD FOR TREATMENT OF INFLAMMATORY JOINT DISORDERS

FIELD OF THE INVENTION

The present invention relates to a method of treatment of inflammation and pain in the joint of a human or animal. The invention further relates to use of monomodal and bimodal molecular weight fractions of dextran for the manufacture of a medicament for such treatment and a dosage unit of such medicament.

BACKGROUND

Inflammatory diseases, which include inflammatory synovitis, arthritis generally, rheumatoid arthritis more specifically, and other diseases including osteoarthritis are leading causes of losses in time and earnings in the United States. More specifically, approximately six million of all arthritis sufferers are afflicted with rheumatoid arthritis. Of these, if past trends continue, over fifty percent (50%) ultimately will have involvement of the knee joint: over eighty percent (80%) will have involvement with the hand joint; and somewhat smaller percentages will have involvement of other joints such as the ankle, elbow, shoulder, hip and wrist.

Rheumatoid arthritis and other forms of inflammatory disease are believed to be autoimmune diseases wherein parts of the body are attacked by antibodies manufactured by the body. These antibodies may be produced in response to viruses present in the body.

A source of disability for the sufferer of rheumatoid arthritis is an inflammatory response, of unknown origin, in the synovium or lining of an afflicted joint. Chronic inflammation of synovial tissues, or synovitis, may lead to pannus formation and, eventually, to destruction of the joint cartilage. Both chronic and acute joint inflammation is generally associated with pronounced pain, which often severely restricts mobility, contact with friends and the community, and undermines the quality of life. Further sources of pain may be the presence of loose, free floating inclusions or fragments of torn synovial tissue ("loose bodies") in the synovial cavity of the joint or extraarticular inflammation in connective or muscle tissues surrounding the joint.

Most chronic joint disorders such as rheumatoid arthritis, psoriatic arthritis and osteoarthrosis are characterized by degradation of the structures in articular cartilage. Also acute inflammation of a joint is often accompanied by destruction of the cartilage, although in most cases this will not develop into the chronically destructive disease. It is not known which factors are crucial for the acutely inflamed joint to either proceed to healing or develop into the chronic process. Examples of diseases involving acute joint inflammation are yersinia arthritis, pyrophosphate arthritis, gout arthritis (arthritis urica), septic arthritis and various forms of arthritis of traumatic etiology.

Treatment with corticosteroids is one of the factors potentially conducive to the destruction of articular cartilage. Corticosteroids have been known for a long time to accelerate the degenerative process in osteoarthrosis. Such a so-called "steroid arthropathy" occurs far too often as an undesirable side effect of intra-articular corticosteroid treatment and can be avoided only by providing for a sufficiently long period of rest after the treatment. "Steroid arthropathy" is characterized by an advanced degree of articular destruction and X-ray detectable changes of the same type as occur in advanced degenerative articular disease. It should be noted however that the actual conditions prevailing in cases of arthritis with severe inflammation of the joint are of a rather more complex character, since in some of these cases injection of corticosteroids appears to have an overall positive effect on the clinical picture Presently, the primary method of treating rheumatoid arthritis is by use of orally ingested or otherwise systemically administered compounds directed at blocking the inflammatory process. These compounds include aspirin, penicillamine, gold salts, corticosteroids and many other ethical drugs. Unfortunately, these attempts are often unsuccessful or associated with unacceptable side effects and the relief provided is temporary at best As mentioned above, some of these therapies such as corticosteroids may induce further deterioration of the joint disorder.

An alternative mode of treatment is to inject anti-inflammatory agents or substances which improve lubrication between surfaces of the joint directly into the synovial cavity of the afflicted joint, thus minimizing the risk of systemic complications.

An example of such an approach is the intra-articular injection of highly viscous or visco-elastic colloids such as high molecular weight hyaluronan (a natural constituent of synovial fluid) or its cross-linked derivatives to cushion and lubricate apposing structures within the synovial cavity. Unfortunately this treatment is not always successful and is very expensive.

Dextran is another biocompatible colloid which has been used for many years as a plasma substitute and expander following blood loss. It is not visco-elastic however and has not previously been used in the joint for treatment of local inflammation.

Dextran is a naturally occurring polysaccharide composed of chains of repeating glucose units and thus typically exists as a mixture of different size molecules whose molecular weights can range from about 300 daltons up to 15 or 20 million daltons. For most clinical purposes however, a molecular weight range of 30,000 to 110,000 daltons is preferred and the two fractions most commonly used for intravenous use have weight average molecular weights (Mw) of 40,000 and 70,000 respectively. These dextran fractions however can cause rare anaphylactic (hypersensitivity) reactions which can be prevented by blocking circulating antibodies to dextran with a very low Mw fraction of dextran (dextran 1,000).

The biological actions of dextran vary considerably with molecular weight. Some properties, such as aggregation of red blood cells by dextrans over 80,000 daltons are completely reversed by dextrans less than 35,000. The size of the molecule also determines its persistence in various body compartments such as the intravascular space or the synovial joint cavity-very small molecules like dextran 1,000 D will diffuse into surrounding tissues and the perisynovial microcirculation much faster than larger molecules such as dextran 70,000 D which have a much longer persistence in, for example, plasma or synovial fluid.

These differences in membrane permeability between very low and higher mol wt dextrans may have relevance in partly explaining the surprising effects disclosed below of different dextran fractions on pain and mobility in inflammatory joint disorders.

In summary, there exists a longfelt need for an effective solution for inflammatory joint disorders. Local administration into the joint offers the advantage of minimizing systemic side effects seen with oral or intravenous drugs. Additionally, however, the solution should provide immediate and sustained relief of pain emanating both from inflamed synovium and cartilage within the joint as well as inflamed tissue in the near vicinity of the joint. The solution should also improve joint mobility and quality of life and should be inexpensive and have a long shelf life. The present invention satisfies these needs and provides related advantages as well.

DISCLOSURE OF THE INVENTION

The present invention is based on the finding that intra-articular injection of clinical dextran into the joint of a patient suffering from an inflammatory joint disorder has the ability to prevent pain and suppress inflammation in and around the said joint.

It is an aspect of the invention to provide effective prophylactic and/or curative pharmacological treatment of an inflamed joint for the relief of pain and prevention of joint damage in a warm-blooded animal including man.

It is another aspect of the invention to provide such treatment for patients in critical conditions such as patients suffering from acute arthritic inflammation and pain, physical trauma, viral or bacterial injury within or in close proximity to the joint and also to provide a vehicle for other pharmacologically active drugs such as anti inflammatory, antibiotic, antiviral, anaesthetic, cytostatic and disease modifying agents.

These aspects, and others set forth more fully hereinbelow are achieved by a method for treating inflammatory joint disorder in a mammal in need of such treatment, which comprises injecting into the joint of the mammal an effective amount of a pharmaceutically acceptable composition comprising a non-toxic amount of clinical grade dextran for treating inflammatory joint disorders in association with a suitable diluent or carrier.

DETAILED DESCRIPTION OF THE PREFERRED EMBODIMENTS

The invention is more specifically based on the finding that when patients acting as their own historical control with longstanding inflammation and pain in an inflamed joint were given an intra-articular injection of monomodal mol wt dextran 70,000, they experienced an unexpected and sustained relief of pain within the joint and marked improvement in joint mobility. More notably, it was found that the addition of dextran 1,000 to the intra-articular injection of dextran 70,000 to form an admixture having a bimodal mol wt dextran composition, provided two additional unexpected beneficial effects, namely, a) a more rapid onset of pain relief and improved joint mobility than that noted after dextran 70,000 alone and b) an extension of the pain relief and suppression of inflammation to adjacent structures and tissues such as muscle and connective tissue outside the joint itself. An additional advantage of the inclusion of dextran 1,000 in the above admixture is its well-documented ability to prevent or minimize the risk of anaphylactic reactions to high mol wt dextrans.

The invention thus provides physiologically acceptable solutions for intra-articular injection comprising mono- or bimodal molecular weight dextrans in a sterile aqueous vehicle, said solutions having a utility in treating patients suffering from inflammatory joint disorders.

Accordingly the invention relates to a method of treatment of inflammatory joint disorders in warm-blooded animals including man, said method comprising intra-articular injection of mono- or bi-modal molecular weight dextran fractions in an amount effective for such treatment.

As used herein, the word "treatment" is used to cover both prophylactic and curative treatment, unless otherwise is apparent from the specific context.

In particular the invention is related to treatment of inflammatory joint disorders brought about by arthritis, osteoarthrosis, physical trauma, bacterial or viral infection, etc, The treatment may be repeated as often as necessary for as long as the risk of pain or inflammation prevails, e.g. every 2 to 24 weeks.

When used in accordance with this invention, the unit dosage form is adjusted to the estimated volume of the synovial space in the afflicted joint. For intra-articular injection it is, of course, essential that the dextran solution is sterile and free from fungi or bacteria.

In a preferred embodiment of the invention, the physiologically acceptable solution comprises a medium mol wt dextran fraction (M) in a concn of 0.21 to 32 percent w/v, preferably 4 to 8% w/v, of the final solution and a very low mol wt fraction (L) in a concn of 0.2 to 6% w/v, preferably 0.6 to 2.4% w/v of the final solution. The weight average weights (Mw) of fractions M and L may vary within wide limits defined by the ranges 30,000 to 110,000 and 500 to 3,000 daltons respectively.

If it is considered suitable to administer a pharmaceutical drug into the inflamed joint, for example to create a local "depot" for slow release, it may naturally be performed by adding the drug to the dextran compositions of this invention. Examples of such additions include local anaesthetics, corticosteroids, antibiotics, etc, etc, as well as agents employed to increase the viscosity or visco-elasticity of the synovial fluid such as carboxymethylcellulose (CMC), hyaluronic acid, chondroitin sulphate or other GAGs.

Naturally the compositions of this invention may contain other physiologically preferable polysaccharides such as CMC, hydroxyethyl starch or glycosaminoglycans (GAGs) so that the above-described properties are achieved even if a minor part of the dextran is thus replaced.

Intra-articular injection can be achieved by any technique known to the art.

The invention furthermore relates to the use of dextran, particularly within the molecular weight limits specified above, for the preparation of compositions for treating inflamed joint disorders, where the contents of dextran components in the composition lie within the above specified ranges.

Apart from dextran, the composition contains water and possibly physiologically preferable salts and buffering agents as, for example, sodium chloride and phosphate buffer.

According to yet a further aspect of the invention, we provide a method for treating inflammatory joint disorders, whereby a dextran composition, as specified above, in a quantity suitable for the actual space in which it is to be administered, is implanted in connection with a surgical operation.

This physiologically acceptable solution is inexpensive to manufacture and is not adversely affected by temperature extremes. As another aspect of the invention, the physiologically acceptable solution is easily administered without pain by a single intra-articular injection.

Other features and advantages of the present invention will become apparent from the following cases which illustrates, by way of example, the principles of the invention.

EXAMPLES OF TREATMENT (note—in the examples below, dextrans 70,000 and 1,000 daltons Mw are denoted "dextran 70" and "dextran1'" respectively.

Example 1

A 50 year old man with a long-standing 15 year history of severe inflammatory arthritis and psoriasis, previously necessitating bilateral amputation of the toes, presented with a very painful right shoulder and rupture of the left biceps tendon with disorganization of the hanging left shoulder joint. He had previously been on high dose oral prednisolone therapy, which was discontinued following development of acute pustular psoriasis, and had also receiving local steroid injections throughout his illness (which may have contributed to the rupture of his biceps tendon.)

Bitter and disappointed, he refused any further steroid injections. In an attempt to slightly expand synovial fluid volume he was offered and consented to intra-articular injection of 5 ml 6% dextran 70 as a "last resort". The dextran injection unexpectedly provided progressive relief of pain and improvement in movement in the treated shoulder joint with major improvement in subjective assessment of quality of life over the following weeks. Two years later, a happy man demonstrated voluntarily a normal shoulder joint with full range of movement and normal X-ray appearance. This improvement has been sustained for an additional 5 years until the present.

Example 2

A 70 year old man with a 10 year history of generalized osteoarthritis, severe diabetic cheiroarthropathy of the hands and vascular disease including progressive claudication and a myocardial infarction 11 years previously, presented with longstanding severe painful arthritis of both knees. Arthroscopy revealed grade 2–3 changes, but no loose body. A knee replacement operation was refused because of his cardiac and vascular condition.

An injection of 5 ml 6% dextran 70 into the right knee progressively reduced the pain and improved movement over the following days. Three weeks later pain returned when some synovial fluid leaked from the joint as the patient knelt on the patella. This pain was later relieved by a further intra-articular injection of 3 ml 6% dextran 70 and the patient again became very active in his garden. The treatment was repeated five months later (5 ml) and again after another six months, each time with relief of pain and improved mobility.

The patient later returned to the orthopaedic surgeon for reassessment for a right knee replacement two years after the first dextran injection. He was then told that there had been such a great improvement in this knee, both clinically and radiologically, that the operation was no longer necessary. X-ray showed osteoarthritis of the right knee with joint spaces well preserved. Following identification of very painful intra-articular loose bodies on two later occasions however, he requested a further injection of dextran, whereby he received easily and painlessly a 5 ml intra-articular injection containing 5.7% dextran 70 and 1.14% dextran 1 into both knees. Surprisingly, pain relief was immediate (within 10 mins) and one week later he was walking freely without pain in his knees and danced a number of high kicks to show the physician his regained full motility.

Example 3

This case was a 75 year old woman with a 25 year history of diabetes and a deformed right foot (talipes equino-varus) Due to regular use of a walking stick, she carried the weight from her right foot through her right arm and shoulder. Over the last seven years she has suffered from painful limited movement in the right shoulder. Movement was restricted to the horizontal level, and she was unable to sleep due to the pain.

The right shoulder joint was slowly injected with 5 ml 6% dextran 70 and pain relief occurred already within 20 minutes. Five days later she could raise the arm to full elevation and sleep without pain. A week later she was doing all the housework. Three months later she was so delighted with the improvement in her right shoulder that she requested and received a dextran injection for the arthritis (confirmed by X-ray) in her deformed right ankle. A week later, she was free from pain and learning to walk correctly on the foot. Revisits to the physician 6 and 24 months later demonstrated excellent function in both of these joints.

Example 4

A 75 year old housewife suffered from chronic psoriasis with polyarthritis. She had developed generalized arthritis at the time of the menopause with degeneration of the spine, particularly the L4/5 disc with osteophyte formation. On presentation she had longstanding severe pain in both knees, particularly the left one, which severely restricted her mobility. X-rays revealed "bitateral osteoarthritis in the knee and particularly of the patellofemoral joints."

Following intra-articular injection of 5 ml of 5.7% dextran 70+1.14% dextran 1 into each knee joint easily and painlessly, she experienced immediate relief of pain and one week later still exhibited free painless movement of both knees and was able to go out to the town to go shopping. She has now maintained this impressive improvement for six months until the present.

Example 5

A 76-year-old obese hypothyroid woman with "marked arthritis" since 1994 sustained an injury to her left foot in 1995 with deep tissue sepsis which had to be excised. She also developed severe pain in the right knee (perhaps due to compensating overuse). X-rays showed further deterioration of the right knee joint, particularly the medial compartment. She was given a 5 ml intra-articular injection of 5.7% dextran 70+1.14% dextran 1 at that time with immediate pain relief. Twelve months later she requested a further injection of bimodal mol wt dextran which was given to both knees. A week later she was able to walk to the town with free painless movement in both knees. A further injection of 5.7% dextran 70+1.14% dextran 1 was given in both knees two years later which gave her free, immediately painless movement and a feeling of confident wellbeing which has been sustained for over 6 months until the present.

Example 6

A 77 year old housewife with a long 20 year history of arthritic changes confirmed by X-ray in her spine, pelvis and hips and with pain in the right arthritic knee underwent arthroscopy and synovial biopsy which revealed active chronic synovitis, a diagnosis of hyperparathyroidism, with chondrocalsinosis. X-ray also revealed a bone cyst. The knee was injected with steroids which gave only temporary improvement. In spite of severe pain and disability, no further hospital treatment was offered. Her condition remained essentially unchanged with severe pain and restricted mobility for seven years until her right knee was injected with 5.7% dextran 70+1.14% dextran 1 easily and painlessly with immediate relief of pain. One week later she still has free movement without pain. She could get out of bed in one movement instead of her previously slow painful routine of easing her legs to the floor taking an hour to do so. She could also walk upstairs herself instead of needing her husband to support her.

Example 7

An 84 yr old headmistress with "severe degenerative changes in her left knee and diminished bone density" on X-ray was treated with etidronate calcium+vitamin D. Because of longstanding pain in her left knee she was given a 5 ml intra-articular injection of 5.7% dextran 70+1.14% dextran 1 with immediate pain relief. During consultation one week later she reported she was now able to walk two miles each day and the dextran injection had given her whole body a sense of "wellbeing" as well as free painless movement of her knee. This improvement was maintained for 2 yrs until an accident with fracture of her right hip (which was pinned & plated) and right wrist brought return of pain. A further injection of 5.7% dextran 70+1.14% dextran 1 again gave immediate relief of pain.

The above Examples demonstrate that intra-articular injection of medium mol wt dextran, especially when combined with a very low mol wt dextran fraction, in patients suffering from a long history of chronic painful joint disorders produces:

a) dramatic (rapid) relief of pain, swelling and lameness in the afflicted joints;

b) sustained improvement in joint function for up to 6 months after the treatment, in many cases enabling patients who were previously unable to walk to have since walked distances of 1 to 2 miles; and c) sustained improvement in the pathophysiology of joint structures as illustrated by objective parameters such as X-ray examination, indicating protection of joint cartilage against degeneration.

Although the invention has been described with reference to the presently preferred embodiment, it should be understood that various modifications can be made by those skilled in the art without departing from the invention. Accordingly the invention is limited only by the following claims.

What is claimed is:

1. A method for treating inflammatory joint disorder in a mammal in need of such treatment, which comprises injecting into the joint of said mammal an effective amount of a pharmaceutically acceptable composition comprising a nontoxic amount of clinical grade dextran for treating inflammatory joint disorders in association with a suitable diluent or carrier.

2. The method of claim 1 wherein said composition comprises 0.2 to 32% w/v of a dextran fraction with average molecular weight between 30,000 and 110,000 daltons in aqueous solution.

3. The method of claim 2 wherein the solution also contains 0.2 to 6% dextran with an average molecular weight between 500 and 3,000 daltons.

4. The method of claim 1 further comprising administering a therapeutically effective amount of an agent selected from the group consisting of corticosteroids, NSAIDs or other anti-inflammatory drugs, local anaesthetics, antibiotics or visco-elastic agents and combinations thereof with dextran for enhancing the effect of dextran in relieving pain and inflammation in and around an inflamed joint.

5. The method of claim 2 further comprising administering a therapeutically effective amount of an agent selected from the group consisting of corticosteroids, NSAIDs or other anti-inflammatory drugs, local anaesthetics, antibiotics or visco-elastic agents and combinations thereof with dextran for enhancing the effect of dextran in relieving pain and inflammation in and around an inflamed joint.

6. The method of claim 3 further comprising administering a therapeutically effective amount of an agent selected from the group consisting of corticosteroids, NSAIDs or other anti-inflammatory drugs, local anaesthetics, antibiotics or visco-elastic agents and combinations thereof with dextran for enhancing the effect of dextran in relieving pain and inflammation in and around an inflamed joint.

7. A method for preparation of an aqueous injectable composition for treating inflammatory joint disorder, comprising including in the composition clinical grade dextran, wherein the dextran has a bimodal molecular weight distribution form, the said composition containing 0.2 to 32% w/v dextran with an average molecular weight between about 30,000 and about 110,000 daltons and 0.2 to 6% w/v dextran with an average molecular weight between about 500 and about 3,000 daltons.

8. A physiologically acceptable composition for intra-articular injection for treating inflammatory joint disorders, said composition comprising clinical grade dextran with a bimodal molecular weight distribution form, the said composition containing 0.2 to 32% w/v dextran with an average molecular weight between about 30,000 and about 110,000 and 0.2 to 6% w/v dextran with an average molecular weight between about 500 and about 3,000 daltons.

* * * * *